United States Patent
Tran et al.

(10) Patent No.: US 12,247,221 B2
(45) Date of Patent: Mar. 11, 2025

(54) HYDROGEL FOR 3D TISSUE ENGINEERING

(71) Applicant: THE ROYAL INSTITUTION FOR THE ADVANCEMENT OF LEARNING / MCGILL UNIVERSITY, Montréal (CA)

(72) Inventors: Simon Tran, Montréal (CA); Joseph Matthew Kinsella, Montréal (CA); Jose Gil Munguia Lopez, Montréal (CA); Yuli Zhang, Montréal (CA); Hieu Michael Pham, Oakville (CA)

(73) Assignee: THE ROYAL INSTITUTION FOR THE ADVANCEMENT OF LEARNING / MCGILL UNIVERSITY, Montréal (CA)

( * ) Notice: Subject to any disclaimer, the term of this patent is extended or adjusted under 35 U.S.C. 154(b) by 0 days.

(21) Appl. No.: 18/059,540

(22) Filed: Nov. 29, 2022

(65) Prior Publication Data

US 2023/0174932 A1    Jun. 8, 2023

Related U.S. Application Data

(60) Provisional application No. 63/285,580, filed on Dec. 3, 2021.

(51) Int. Cl.
*C12N 5/071* (2010.01)

(52) U.S. Cl.
CPC ........ *C12N 5/0633* (2013.01); *C12N 2500/14* (2013.01); *C12N 2500/84* (2013.01); *C12N 2513/00* (2013.01); *C12N 2533/54* (2013.01); *C12N 2533/74* (2013.01); *C12N 2537/10* (2013.01)

(58) Field of Classification Search
CPC .............. C12N 5/0633; C12N 2500/14; C12N 2500/84; C12N 2533/54; C12N 2533/74; C12N 2537/10
See application file for complete search history.

(56) References Cited

U.S. PATENT DOCUMENTS 6,991,652 B2 *   1/2006   Burg ...................... A61L 27/50
                                                    623/23.72

OTHER PUBLICATIONS

Liu, S., et al., "Designing vascular supportive albumen-rich composite bioink for organ 3D printing," J Mech Behav Biomed Mater 104: 103642. doi: 10.1016/j.jmbbm.2020.103642. Epub Jan. 20, 2020. (Year: 2020).*
Ozdemir et al., "Biomaterials-based strategies for salivary gland tissue regeneration," Biomater Sci 4(4): 592-604. doi: 10.1039/c5bm00358j. Epub Feb. 15, 2016. (Year: 2016).*
Barros, A., et al., "Development of alginate-based hydrogels/cryogels by gelation under pressure," Tissue Engineering and Regenerative Medicine International Society—EU Meeting 2014 Genova, Italy. (Year: 2014).*
Bai, M.Y., et al., "Shape-Controlled Synthesis of Multicomponent-Encapsulating Alginate Microparticles: Peanut-, Spherical-, and Disc-Shaped Transformations," Chem. Sel. 5, 7797-7802. (Year: 2020).*
Hughes et al. "Matrigel: A complex protein mexture required for optimal growth of cell culture", Proteomics, vol. 10, 2010, pp. 1886-1890.
Kaipparettu et al., "Novel egg white-based 3-D cell culture system", BioTechniques, vol. 45, 2008: pp. 165-168 and pp. 170-171.
Mousseau et al., 2014, "In vitro 3D angiogenesis assay in egg white matrix: comparison to Matrigel, compatibility to various species, and suitability for drug testing", Laboratory Investigation vol. 94, 2014, pp. 340-349.

* cited by examiner

*Primary Examiner* — Tracy Vivlemore
*Assistant Examiner* — Eric J Rogers
(74) *Attorney, Agent, or Firm* — NORTON ROSE FULBRIGHT CANADA LLP

(57) ABSTRACT

It is described a composite hydrogel containing egg white and alginate (EWA) polymers, and a method of producing same, wherein the alginate is cross-linked using frozen calcium chloride disks, creating a scaffold for cells comprising a slow-rate ions diffusion through the matrix, ensuring a homogenous crosslink and smooth surface.

12 Claims, 3 Drawing Sheets

HYDROGEL FOR 3D TISSUE ENGINEERING

CROSS-REFERENCE TO RELATED APPLICATION

The present application is claiming priority from U.S. Provisional Application No. 63/285,580 filed Dec. 3, 2021, the content of which is hereby incorporated by reference in its entirety.

TECHNICAL FIELD

It is provided a composite hydrogel composition containing egg white and alginate (EWA) polymers.

BACKGROUND

Patients treated with radiotherapy for head/neck cancer (≈500,000 new patients annually worldwide) and patients with Sjögren's syndrome (the $2^{nd}$ most prevalent autoimmune disease) experience decreased saliva flow due to the loss of salivary gland (SG) function. SG hypo- or dysfunction results in speech and swallowing difficulties, dry mouth, altered taste perception, dental caries, oropharyngeal infections, and mucositis. Current treatments are only palliative and consist of sipping water constantly, using oral moisturizing products, or pharmaceutical agents to stimulate the remaining acinar cells to produce saliva. The use of three-dimensional (3D) culture that simulates the native cell/organoid microenvironment is a reliable strategy to study ex vivo cellular biology aiming at treatments for diseases. A critical challenge in 3D organoid culture is the development of an appropriate scaffold for specific cells where the microenvironment allows the cells to reorganize into a functional organoid inducing cells to proliferate, migrate, and differentiate.

Hydrogels have been used for a variety of biomedical applications, including being among the most common scaffolds for tissue engineering. Hydrogels are polymers capable of holding high quantities of water (more than 75% w/v) inside of their 3D structure; they are widely used to create 3D scaffolds as a synthetic surrogate for the native cell's ECM. Hydrogels provide ideal cellular microenvironments for cell proliferation and differentiation due to their highly hydrated environments, resemblance to natural anatomy, and cross-linked networks providing porosity. Natural polymers, derived from sources such as algae, animals, and micro-organisms, have frequently been used to make hydrogel scaffolds for tissue-engineering applications owing to their biocompatibility, inherent biodegradability, and anchoring sites allowing cells to attach to their surfaces to drive cell division, adhesion, and migration in a 3D environment. When compared with natural polymers, synthetic polymers derived either from lactic acid, caprolactone, or glycoside monomers, possess more reproducible chemical, mechanical, and physical properties, which are critical for the fabrication of tissue-engineering scaffolds. However, a setback for synthetic polymers is that they lack adhesion sites necessary for cell adhesion, migration, and differentiation. Recently, bioactive synthetic hydrogels have emerged as promising hydrogel scaffolds because they can be molecularly tailored with block structures, molecular weights, mechanical strength, and biodegradability, in addition to their ability to mimic the natural ECM to provide a desirable cellular environment for supporting cell growth.

Based on the chemical properties of hydrogels, they can be classified as follows: (a) homopolymeric hydrogels, comprised of a single species of monomer, which is a basic structural unit employed to build the polymer network. Homopolymers may have a crosslinked skeletal structure depending on the nature of the monomer and polymerization technique. (b) Copolymeric hydrogels, comprised of two or more different monomer species with at least one hydrophilic component, arranged in a random, block, or alternating configuration along the chain of the polymer network. (c) Multipolymer interpenetrating polymeric hydrogel (IPN), is made of two independents crosslinked synthetic and/or natural polymer components, contained in a network form. In a semi-IPN hydrogel, one component is a crosslinked polymer while another component is a non-crosslinked polymer that remains trapped within the 3D structure.

Except for supporting cell immobilization and growth factor delivery, hydrogels have great potential to be "smart" scaffolds, which can be remotely controlled by external stimuli such as temperature, ionic strength, or enzymatic environment. Among all the hydrogels, the current gold standard for 3D culture scaffold is Matrigel, a protein-based ECM extracted from Englebreth-Holm-Swarm tumors in mice, comprised of laminin, collagen IV, and enactin which costs around $16/ml (Hughes et al., 2010, Proteomics, 10: 1886-1890). Considering that traditional 3D cell culture requires at least 10 ml/sample, the total expenses increase exponentially.

Thus, there is still a need for a cost effective and biocompatible hydrogel alternative to be used as 3D culture scaffolds.

SUMMARY

It is provided a hydrogel composition comprising egg white and alginate.

In an embodiment, the egg white and alginate are cross-linked with calcium chloride.

In a further embodiment, the composition comprises 1% to 3% alginate.

In another embodiment, the composition comprises 1%, 1.5%, 2%, 2.5% or 3% alginate.

In an embodiment, the calcium chloride is a $CaCl_2$ solution.

In an embodiment, the $CaCl_2$ solution is at a temperature of 4° C. to 25° C.

In another embodiment, the $CaCl_2$ solution is a frozen $CaCl_2$ solution.

In a supplemental embodiment, the composition is a scaffold.

In an embodiment, the composition further comprises seeded cells on the scaffold.

In an embodiment, the cells are salivary gland cells.

In an embodiment, the composition further comprises a copolymer.

In another embodiment, the copolymer is at least one of gelatin, hyaluronic acid, collagen, laminin and carbon nanotubes.

It is further provided a method of producing a hydrogel composition comprising the steps of providing egg whites; mixing the egg whites with alginate creating an egg white/alginate (EWA) hydrogel; adding the EWA hydrogel on a surface; and incorporating a crosslinker into the EWA hydrogel for crosslinking the alginate in said EWA hydrogel.

In an embodiment, the EWA hydrogel is crosslinked at cold temperature.

In another embodiment, the EWA hydrogel is crosslinked at a temperature of −20° C. to 25° C.

In a further embodiment, the crosslinking of said alginate in said EWA hydrogel occurs at 37° C.

In an embodiment, the EWA hydrogel is a scaffold.

In another embodiment, the surface is a plate.

In an embodiment, the surface is a 6-well plate.

In an embodiment, the method described herein comprises adding the EWA hydrogel into each well of the 6-well plate and placing frozen $CaCl_2$ disks on top of the EWA-hydrogel containing 6-well plate crosslinking said EWA hydrogel forming the scaffold.

In another embodiment, the frozen $CaCl_2$ disks were produced by placing sterile aluminum foil sheets in each well of a 6-well plate, adding a $CaCl_2$ solution into each of the aluminum-coated well, freezing the $CaCl_2$ solution, and the frozen $CaCl_2$ solution forming disks where the aluminum foils peeled away.

In an embodiment, the method described herein further comprises the step of seeding cells on top of the scaffold.

In a further embodiment, the egg whites are mixed with 1% to 3% alginate.

In an embodiment, the egg whites are mixed with 1%, 1.5%, 2%, 2.5% or 3% alginate.

In another embodiment, it is further encompassed a method of expanding cells on a scaffold comprising the steps of seeding cells on a hydrogel composition as defined herein, and culturing and expanding said cells.

In an embodiment the expanded cells are transplantable or injured.

In an embodiment, the expanded cells are injured by irradiation.

BRIEF DESCRIPTION OF THE DRAWINGS

Reference will now be made to the accompanying drawings.

DETAILED DESCRIPTION

In accordance with the present description, it is provided a composite hydrogel containing egg white and alginate (EWA) polymers using a nonconventional method to crosslink the alginate employing frozen calcium chloride disks.

This crosslinking method provided herewith allows creating a scaffold for cells comprising a slow-rate ions diffusion through the matrix, ensuring a homogenous crosslink and smooth surface compared with the traditional hand drop method. The formulation of the composite provided herewith can be tailored to modify the stiffness of the material, which can be suitable for multiple biomedical applications. This composite hydrogel promotes the formation of salivary organoids controlling their sizes.

Hydrogels have been used for a variety of biomedical applications; in tissue engineering, it is commonly used as scaffolds to cultivate organoids in a three-dimensional (3D) environment. EWA as described is a novel hydrogel which combines the advantages of both egg white and alginate; the egg white material provides extracellular matrix (ECM)-like proteins that can mimic the ECM microenvironment, while alginate can be tuned mechanically through its ionic cross-linking property to modify the scaffold's porosity, strength, and stiffness.

It is described a frozen calcium chloride ($CaCl_2$) disk technique to homogenously crosslink alginate and egg white hydrogel is presented for 3D culture of human salivary cells. Different EWA formulations were prepared and biologically evaluated as an organoid platform. Although all five EWA hydrogels showed biocompatibility, the EWA with 2.0% alginate presented the highest cell viability, while EWA with 3% alginate promoted the formation of larger size salivary organoids.

Figure 1:
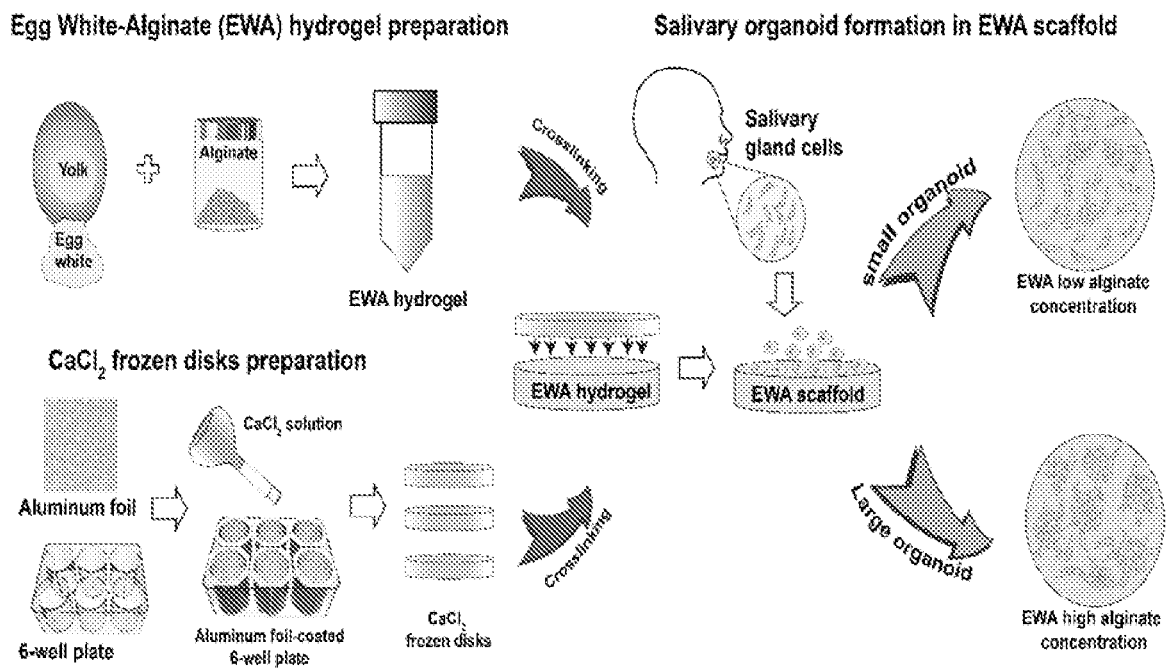
FIG. 1 illustrates a schematic representation of the EWA hydrogel preparation, frozen $CaCl_2$ disk, and salivary gland organoid formation in accordance to an embodiment.

As seen in FIG. 1, the use of frozen $CaCl_2$ disks allows alginate and EW to crosslink in a more controlled manner through the slow diffusion of $Ca^{2+}$ ions. This technique improves the smoothness of the EWA hydrogel surfaces as well as significantly reduces the formation of macro pits and bubbles generated by the addition of the $CaCl_2$ solution using a slow-dispensing micro-pipetting technique. Furthermore, the use of frozen $CaCl_2$ disks allow for better cell distribution across the EWA scaffold surface due to the steady homogenous crosslink. Increasing the alginate concentration in the EWA scaffold, SG organoid formation is promoted with high cell viability.

Alginate is an inert carbohydrate copolymer comprised of 1-4 linked β-D-mannuronic acid (M) and α-L-guluronic acid (G) isolated from brown seaweed and some bacterial species. Divalent ions (e.g. $Ca^{2+}$, $Ba^{2+}$, $Sr^{2+}$) are used as a crosslinker to form an "egg-box" structure by the interaction with blocks of G monomers, producing a stiff and stable 3D structure, thus allowing mechanical modification of the alginate's properties to mimic the ECM stiffness of particular tissues. Alginate is purified by a multi-step extraction procedure yielding high-quality materials that are inert in mammals. It has been shown that no significant inflammatory response is observed when gels formed from commercially available, highly purified alginate are subcutaneously injected into mice.

Egg white (EW) is a viable scaffold due to its great advantages in cellular attachment, differentiation, and proliferation. EW is comprised of an albumen layer which is mainly composed of ovalbumin (<50%) and other structural proteins that resemble ECM proteins (such as collagen), acting as a substrate for cellular attachment. All these EW proteins make EW a great candidate to be used as complementary material in alginate hydrogels allowing the creation of 3D microenvironments that mimic native mammalian ECM.

EW-based biomaterials have been proven advantageous in tissue engineering: (i) it can provide sufficient nutrition for chicken gametes to grow into a baby chick; (ii) its transparency makes it convenient to monitor and record the changes in cell morphology; and (iii) it is inexpensive and widely available. A study reported that epithelial breast tumor cell lines grown on EW have comparable phenotypes as those grown on Matrigel (Kaipparettu et al., 2008, Biotechniques, 45: 165-8, 170-1). Similar observations were found in a study comparing human umbilical vein endothelial cells grown on EW and Matrigel (Mousseau et al., 2014, Lab Invest, 94: 340-349). These studies highlight the feasibility of using egg white as an alternative biomaterial to Matrigel.

One challenge for EWA hydrogels is the instantaneous formation of gels when cross-linked via divalent ion solutions at room temperature, which produces gels that have rough surfaces and is also highly heterogeneous, in addition to their properties being difficult to control. The use of frozen alginate or calcium/solvent solution is proposed as a methodology to create more homogeneous cross-linked hydrogels. The fluidity of EWA decreases with decreasing temperature, thus, a more homogeneous hydrogel can be maintained with the 3D structure that was originally intended.

It is also encompassed that the described EWA can further comprise in combination a copolymer such as for example, and not limited to, gelatin, hyaluronic acid, collagen, laminin, and carbon nanotubes.

FIG. 1 shows the general protocol followed to create EWA scaffolds using frozen $CaCl_2$ disks as the crosslinker, and the formation of salivary gland organoids. Egg white material is extracted from eggs and mixed with different concentrations of alginate to create various EWA hydrogels. For crosslinking, wells from a 6-well plate are covered with sterile aluminum foil, $CaCl_2$ solution is added and incubated at −20° C. overnight. In another 6-well plate, EWA is added, and then frozen disks are placed on the top to crosslink it. Next, salivary gland cells are seeded on the top of the EWA scaffolds and incubated for 7 to 10 days allowing the formation of organoids.

Calcium chloride is one of the most common crosslinkers used in alginate gelation, which has less cytotoxicity compared to other divalent ionic crosslinkers such as $Ba^{2+}$. These divalent cations cooperatively interact with blocks of G monomers to generate ionic bridges between different polymer chains of alginate that entraps water eventually forming a hydrogel. It has been shown that the gelation rate of alginate increased with temperature, while low temperatures reduce the diffusion rate of $Ca^{2+}$ ions, leading to a slower crosslinking process which generates a more ordered network structure, and hence enhanced mechanical properties. This is crucial because for tissue engineering scaffolds, structural uniformity is important not only for well-controlled material properties but also for uniform cell distribution.

At first, $CaCl_2$ was added to the EWA solution by slowly pipetting the crosslinking solution directly onto the EWA. Despite dropping it carefully and slowly, pits and bubbles were inevitably produced on the surface of the EWA (see FIGS. 2a and c). The size and depth of those pits varied and was extremely challenging to make uniform. This heterogeneity in the material macro-porosity often resulted in higher cell density at the bottom of the pits where they clumped together while the flat surfaces had sparse amounts of cells. This could ultimately be the result of gravity, causing cells to slide down along the sidewalls of pits before they firmly attach to the scaffold.

Figure 2:
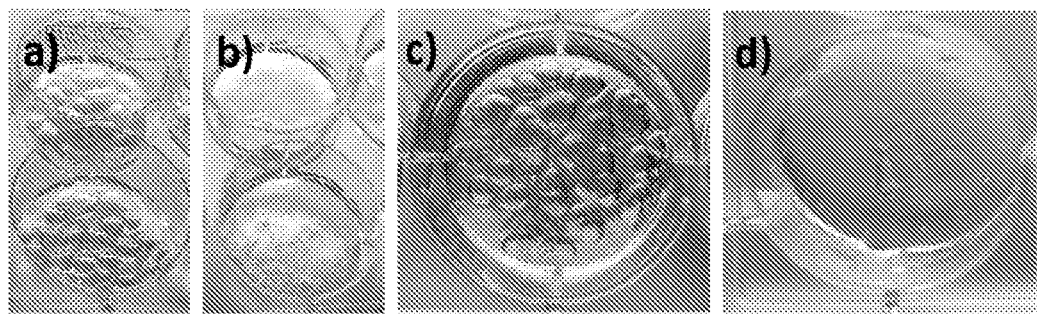
FIG. 2 illustrates images of EWA made by two techniques, and the small bubbles in EWA, wherein the EWA images were acquired before (a, c) and after (b, d) the improved crosslinking technique, c) and d) show one well from the 6-well plate where the low quantity of micro and macro bubbles/pit is observed on the improved method (d).
Figure 3:
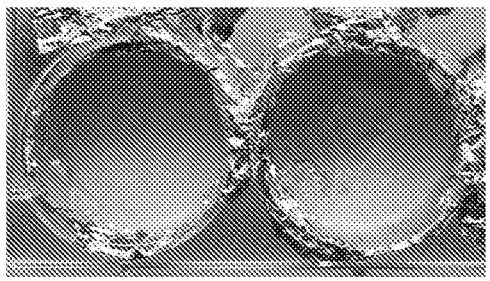
FIG. 3 illustrates frozen $CaCl_2$ on aluminum foil pressed against the interior of the wells of a 6-well plate.

EWA was fabricated with smoother surfaces by placing frozen $CaCl_2$ disks (see FIG. 3) on the surface of the hydrogel, allowing a slow-rate crosslinking process as the $CaCl_2$ disk thawed. This method allows the formation of a smoother, uniform EWA surface (FIG. 2C and d) with a visibly lower amount of bubbles within the scaffold (FIG. 2d). It is believed that the two main reasons leading to this improved outcome are: (a) the low temperature of crosslinking solution, which ensures the homogenous and slow-rate crosslink due to the slow release of $CaCl_2$ molecules as the disk thaws; (b) the smooth surface created in the bottom surface of the frozen $CaCl_2$ disks that is in direct contact with the EWA surface. After the improvement in crosslinking technique, it was observed that cells and cell clumps were homogeneously distributed across the hydrogel. This improvement on EWA surface smoothness could provide more reliable results, driven by better cell distribution and cellular attachment to the scaffold.

Another challenge with using EWA is that EWA scaffolds shrink slightly during the crosslinking process due to the reorganization of the alginate chains to form a stiffer structure. An average of 15% decrease in size of the EWA scaffolds post-crosslinking was noted, creating spaces between the hydrogel and the walls of the 6-well plate. The smaller scaffold size allows cells to be displaced off of the scaffold and instead attach to the bottom of the wells during the initial cell-seeding phase. As a result, for all cell experiments, wells that contained EWA without gaps were only included.

Figure 4:
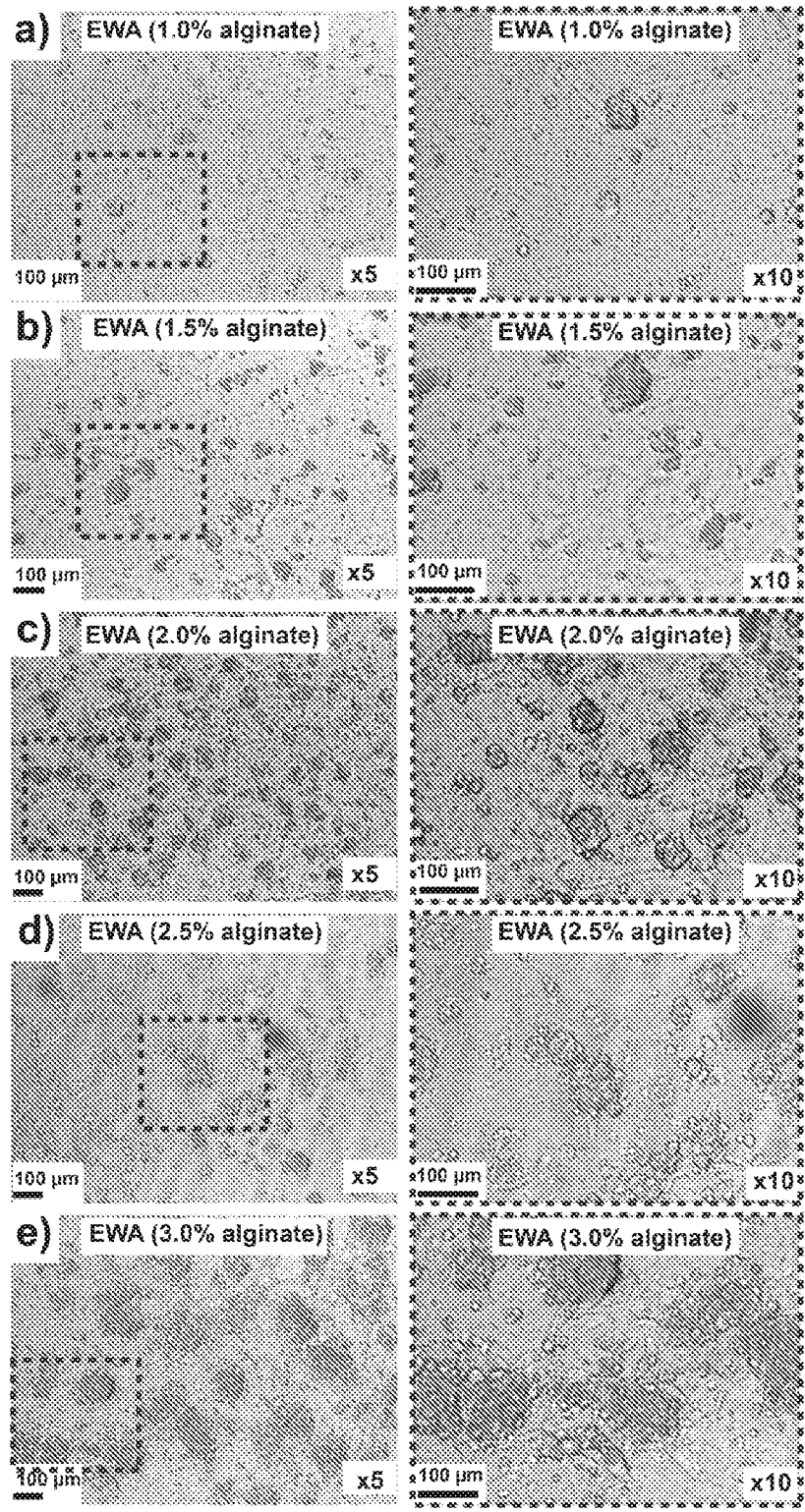
FIG. 4 illustrates optical images of NS-SV-AC cells growing on EWA hydrogels at day 3 after culture wherein cells were seeded on top of the EWA at various concentrations of alginate: 1.0% (a), 1.5% (b), 2.0% (c), 2.5% (d) or 3.0% (e), and magnification ×5 (left panel) and ×10 (right panel) are presented, and scale bar 100 μm. Dotted lines show the area of the magnified images.

Several studies have demonstrated that some mammalian cells are able to form organoids or spheroids in 3D culture, whether the cells are embedded in the hydrogel or seeded on the scaffold. The ability of five different formulations of EWA on the SG organoid formation was evaluated. FIG. 4 shows the organoid formation of the NS-SV-AC cell line seeded on EWA at day 3. Using 1% alginate, most of the cells were attached to the EWA surface and spread as a monolayer, just a few organoids were observed on the cultures (FIG. 4a). In the case of EWA with 1.5% alginate, more organoid-like structures were visible (FIG. 4b). This observable trend appears to continue with the increase of alginate percentage in the final EWA biomaterial, with 3% alginate showing the most numbers of organoids (see FIGS. 4c, d and e). These results suggest that alginate concentration promotes the NS-SV-AC organoid formation. As observed, scaffolds with a higher concentration of alginate formed larger organoids and their sizes increased with increasing alginate concentration.

Figure 5:
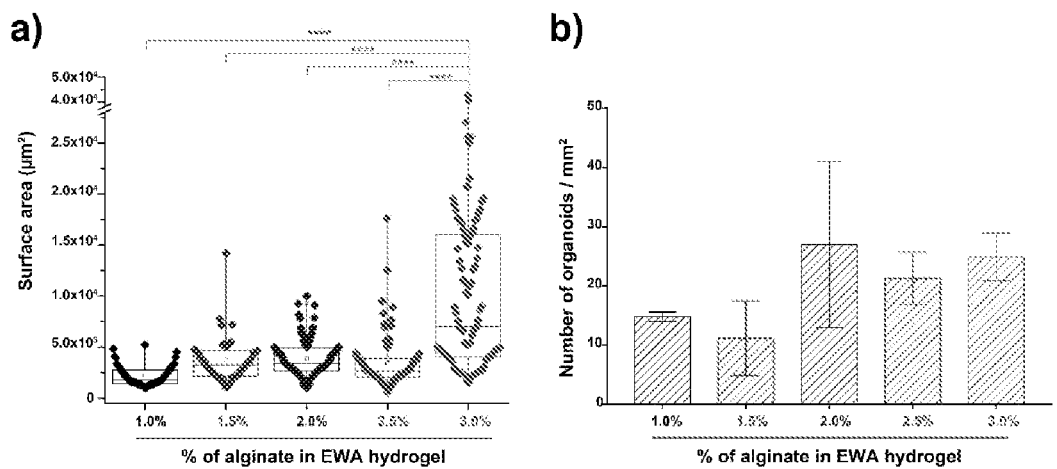
FIG. 5 illustrates surface area and distribution of organoids formed on EWA hydrogels, showing in (a) the surface area ($\mu m^2$) of each organoid found in the EWA hydrogels as measured and compared among EWA containing different alginate percentages, data were plotted as boxplot using a box limit of $25^{th}$ and $75^{th}$ percentiles with a minimum-maximum whisker's range; ****$P<0.0001$; and in (b) the number of organoids per square millimeter in the EWA scaffolds determined and compared among the different alginate concentration samples, where data are presented as mean±SD, n<3.

Following the characterization of the organoid formation in EWA, the surface area of the organoids in each hydrogel was measured. The measure of surface area is used as an additional parameter to determine the efficiency of the hydrogels in promoting organoid formation in 3D structures. FIG. 5 shows the organoid sizes and distribution in different EWA blends. EWA 1% produces organoid no larger than $5 \times 10^3$ $\mu m^2$; increasing the concentration of alginate in the EWA material resulted in larger organoid formation (FIG. 5a). No significant differences among EWA 1% to 2.5% in mean surface area was observed; however, the EWA 3% hydrogel showed significant differences when compared with the rest of the EWA material, where organoid sizes ranged from $5\times10^3$ µm² to $4\times10^4$ µm² (FIG. 5a).

Organoid/spheroid sizes were classified based on surface area: small (500-10,000 µm²), medium (10,000-20,000 µm²), and large (>20,000 µm²). The formation of a few medium size organoids was seen (between 1 and 3) in 6-well plates containing EWA 1.5%, 2.0%, and 2.5% samples, but found higher amounts of medium and large-sized organoids in the wells containing EWA 3.0%. These results suggest that higher concentrations of alginate in EWA hydrogels promotes the formation of larger organoids.

The number of organoids per square millimeter was quantified. No significant differences among the five EWA samples was found, however, the number of organoids/mm² in EWA 2.0% was slightly larger than the others (FIG. 5b). These differences in organoid sizes and quantities could be related to the mechanical properties provided by the alginate concentration in the scaffolds, where the stiffness of the scaffold plays an important role in cell growth, migration, and survivability.

Figure 6:
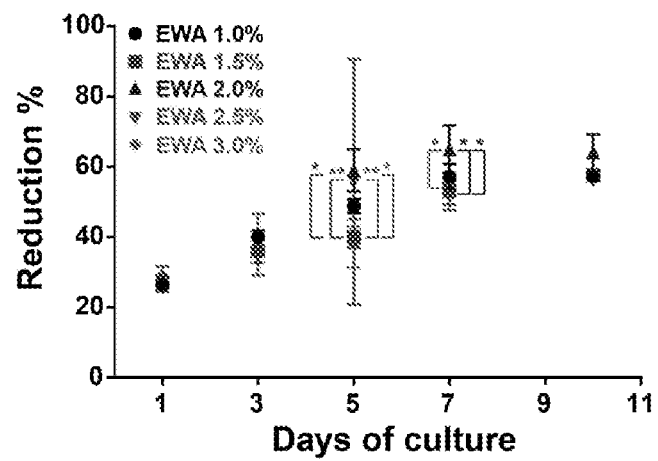
FIG. 6 illustrates the growth rates of NS-SV-AC seeded on EWA at 1, 1.5, 2, 2.5, or 3% alginate, wherein data are presented as mean±SD, n≤3, *$P<0.05$, **$P<0.01$.

To determine the viability of the cells and organoids cultured in the EWA material, a cell viability test was performed using an AlamarBlue assay. AlamarBlue monitors the reducing environment of the living cell. The active ingredient is resazurin (IUPAC name: 7-hydroxy-10-oxidophenoxazin-10-ium-3-one); it is non-toxic which allows for continuous monitoring of cells in culture over multiple time points. As the indicator dye accepts electrons, it can be reduced by NADPH, FADH, FMNH, NADH, and cellular cytochromes, thus changing from the oxidized, non-fluorescent, blue state to the reduced, fluorescent, pink state. Therefore, the change from oxidized to reduced state, a measure of cellular activity, can be quantitatively measured as colorimetric and/or fluorometric readings, where more detection of reduction reflects higher cell viability. First, NS-SV-AC cells were seeded on EWA containing either 1%, 1.5%, 2%, 2.5%, or 3% alginate. Then the samples were cultured for 10 days, taking samples at 1, 3, 5, 7, and 10 days after the initial seeding period (day 0). FIG. 6 shows the growth rates of NS-SV-AC cells seeded on EWA. The viability and proliferation increased over time in all samples from day 1 to day 7, slowing down thereafter, likely contributable to either the formation of large organoids or the number of cells/organoids nearing the maximum growth capacity of the scaffold volume. On day 5, the cell viability of EWA 2.0% and 2.5% alginate showed significantly higher values than the EWA 1.5% and 3.0%. Additionally, on day 7, only the EWA 2% hydrogel showed higher cell viability than the other samples. This result suggests that EWA hydrogels promoted the proliferation of NS-SV-AC as well as their viability, but the EWA with 2% alginate showed the greatest cell viability and proliferation.

Accordingly, it is provided that a smoother surface in the EWA hydrogel can be generated by decreasing the cross-linking rate using a frozen $CaCl_2$ solution. In addition, salivary gland organoid formation can be controlled by modifying the concentration of alginate in the EWA material. Visual differences in organoid formation across five different EWA groups are evident, showing that the 2%, 2.5%, and 3% alginate groups of the EWA material are the better hydrogels for promoting cell self-assembly, with high cell proliferation and cell attachment.

As further encompassed, the provided scaffold can be used as an alternate 3D culture scaffold for studies on drug-screening, cell-migration, or as an in vitro disease model. In addition, the provided EWA can be used as a potential source for cell transplantation. The low cost of producing EWA is an added advantage. Using egg white-based hydrogels as described herewith promotes cells reorganization as spheroids, suggesting that using primary cultures of cells or stem cells, it is possible to promote salivary organoids in EWA. Spheroid and organoid structures can be injured (e.g. irradiation-injury) in order to create an in vitro disease model that mimics the in vivo injury-damaged salivary glands after irradiation (e.g. radiotherapy). By having this in vitro irradiation-injury model, the efficacy of newly developed or current drugs/therapies (for example, medicines for xerostomia, dry mouth) can be tested directly on these functional salivary spheroid structures to determine cell response (e.g. viability) and function. Furthermore, this in vitro model can be used in the study of cell migration because of its transparent property, which supports the use of optical microscopes, as cells live and move within the gel just as they do in vivo. In addition, EWA can support organoid generation, is biodegradable and is not immunogenic, and it can then be used as a platform to culture and expand salivary cells for cell transplantation. For example, it is encompassed to transplant salivary organoids grown in EWA into the site of the damaged salivary glands.

Example I

Fabrication Procedure and Testing of EWA

Egg White Isolation and Heat Treatment

Fresh eggs (Large White Eggs Omega-3) were purchased from a local retail store (Montreal, QC, Canada). Eggs were sprayed with 70% ethanol then were decontaminated under a biological safety cabinet (BSC). The apex of the shells was cracked and removed (an approximately 1 cm diameter hole was created). Then, the EW material was poured into a 50 ml conical centrifuge tube using forceps to pull the EW out, ensuring no visible contamination from the egg yolk; all other contents (chalaza, yolk, and watery content) were discarded. Each egg harvested provided approximately 25 ml of EW. Next, the tubes were placed in an incubator at 58° C. for 1 hour to sterilize the EW material (pasteurize).

Egg White-Alginate Hydrogel Preparation

Sodium alginate (Protanal LF 5/60, FMC BioPolymer) solutions (1%, 1.5%, 2%, 2.5%, and 3%) were prepared by dissolving the alginate into 1:3 Hank's Balanced Salt Solution (HBSS) (GIBCO, 14025076)/Epi Max, following by shaking manually ten times. Then, the tube was placed on a Speci-Mix Aliquot Mixer (Thermolyne, M71015) in a 37° C. incubator for approximately 30 min for further dissolution. The samples were stored at 4° C. until use. A crosslinking solution was prepared by dissolving 90 mM calcium chloride ($CaCl_2$) (Fisher Scientific, C77-500) in sterile double distilled water ($ddH_2O$) under a BSC.

To create the EWA, EW was poured together with sodium alginate (1%, 1.5%, 2%, 2.5%, or 3% w/v) solutions (2:1) into a 50 mL conical tube. The mixture was homogenized by pipetting. Once homogenous, the EWA mixture was centrifuged at 300 g×3 min at 4° C. to eliminate bubbles from the solution; the bubble foam produced on the surface was discarded. 2 ml of the EWA solution was placed into each well of a 6-well plate. Each well containing EWA was cross-linked with 90 mM $CaCl_2$ solution as follows: sterile aluminum foil sheets were placed to line the bottom of each well. Next, 3 ml of $CaCl_2$ solution was added into each aluminum-coated well. The plate was then placed in a freezer at −20° C. for 6 h to freeze the $CaCl_2$ solution. Once frozen, the frozen $CaCl_2$ disks were removed from the plate and all aluminum foils were peeled away. Finally, the frozen $CaCl_2$ disks were gently placed on the top of the EWA-coated 6-well plate, allowing the melting process to occur at 37° C. and crosslink over 12 h to create the 3D EWA scaffold. Excess $CaCl_2$ solution was aspirated and the EWA scaffolds were rinsed with PBS. All procedures were performed under sterile conditions.

Biological Testing

The normal salivary simian virus 40-immortalized acinar cells (NS-SV-AC) were cultured at 5% $CO_2$, 37° C. in Epi Max culture medium (Wisent Bio Products, 002-010-CL) supplemented with antibiotic-antimycotic (100 μg/mL penicillin, 100 μg/mL streptomycin, and 0.25 μg/mL amphotericin B) (Thermo Fisher, 15240062) in a culture petri dish (Sarstedt). Then, the NS-SV-AC culture was rinsed twice with sterilized PBS and the cells were detached with 0.05% Trypsin (GIBCO, 25200-056) when confluency reached 90%. All biological testing with cells were performed between the $3^{rd}$-$6^{th}$ cell passage. 50,000 cells/well were seeded into EWA-coated plates at 5 different concentrations of alginate (1%, 1.5%, 2%, 2.5%, and 3% w/v). Then, they were cultured with Epi Max growth medium at 37° C., 5% $CO_2$ for 7 days; the culture medium was replaced with fresh medium every 2 days. Samples were taken on day 1, 3, 5, 7 and 10, where cell viability was measured using the AlamarBlue Cell Viability Reagent (Invitrogen, DAL1025). For each well, 1.5 ml culture medium was replaced with 1.5 ml of the AlamarBlue solution. EWA-coated wells without cells were used as a control. Samples were protected from light and incubated at 37° C. and 5% $CO_2$ for 8 hours. The oxidation-reduction of the AlamarBlue reagent was analyzed by absorbance measurements at 562 nm and 595 nm wavelengths using 100 μl of the solution from each well and a microplate reader (Bio-Tek Instruments, EL800). All experiments were performed in triplicate for every time point. NS-SV-AC organoid formation was tracked by optical microscopy using a Leica DM IL microscope at ×5 and ×10 magnifications.

Statistical Analysis

All test samples were performed in triplicate. Data are presented as mean±SD. One-way ANOVA was performed with a Tukey's post hoc test with a P value<0.05. Data from the surface are were plotted as Boxplot graphs using the Origin Pro 9 software, with a box limit of $25^{th}$ and $75^{th}$ percentiles and a minimum-maximum whisker's range.

While the disclosure has been described in connection with specific embodiments thereof, it will be understood that it is capable of further modifications and this application is intended to cover any variations, uses, or adaptations including such departures from the present disclosure as come within known or customary practice within the art and as may be applied to the essential features hereinbefore set forth, and as follows in the scope of the appended claims.

What is claimed is:

1. A scaffold composition comprising egg white, calcium chloride ($CaCl_2$ and alginate, and wherein the $CaCl_2$ is in a solid state and wherein the alginate is in a fluid state.

2. The composition of claim 1, comprising 1% to 3% alginate.

3. The composition of claim 1, further comprising a copolymer.

4. The composition of claim 3, wherein the copolymer is at least one of gelatin, hyaluronic acid, collagen, laminin and carbon nanotubes.

5. A method of producing a hydrogel composition using the scaffold composition of claim 1 comprising the steps of:
   a) providing egg whites;
   b) mixing the egg whites with alginate creating an egg white/alginate (EWA) hydrogel;
   c) adding the EWA hydrogel on a surface; and
   d) incorporating a solid $CaCl_2$ that is a frozen solution into the EWA hydrogel which is in a fluid state for crosslinking the alginate in said EWA hydrogel.

6. The method of claim 5, wherein the EWA hydrogel is crosslinked at a temperature of −20° C. to 25° C.

7. The method of claim 5, wherein the EWA hydrogel is a scaffold.

8. The method of claim 5, wherein the surface is a plate or a 6-well plate.

9. The method of claim 7, further comprising the step e) of seeding cells on top of the scaffold.

10. The method of claim 9, wherein the cells are salivary gland cells.

11. The method of claim 5, wherein the egg whites are mixed with 1% to 3% alginate.

12. The composition of claim 1, wherein the solid $CaCl_2$ is a frozen CaCl2 disk.

* * * * *